United States Patent [19]
Green

[11] Patent Number: 5,955,439
[45] Date of Patent: *Sep. 21, 1999

[54] PHARMACEUTICAL AEROSOL CONTAINING AT LEAST ONE SUGAR

[75] Inventor: Alexander Peter Green, Ware, United Kingdom

[73] Assignee: Glaxo Group Limited, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/849,538

[22] PCT Filed: Dec. 22, 1995

[86] PCT No.: PCT/EP95/05085

§ 371 Date: Jun. 24, 1997

§ 102(e) Date: Jun. 24, 1997

[87] PCT Pub. No.: WO96/19968

PCT Pub. Date: Jul. 4, 1996

[30] Foreign Application Priority Data

Dec. 24, 1994 [GB] United Kingdom .................... 9426252

[51] Int. Cl.$^6$ .......................... A01N 43/04; A61K 31/56; A61K 31/70
[52] U.S. Cl. ............................ 514/23; 514/174; 514/178; 514/180; 514/357; 514/653; 514/757; 514/758; 514/759; 424/45; 424/46; 424/489; 424/499; 604/890.1

[58] Field of Search ..................... 514/759, 178, 514/23, 758, 174, 180, 653, 357; 424/45, 46, 489, 499; 604/890.1

[56] References Cited

FOREIGN PATENT DOCUMENTS

| | | |
|---|---|---|
| 2091713 | 9/1993 | Canada . |
| 2 136 704 | 5/1995 | Canada . |
| 260241 | 3/1988 | European Pat. Off. . |
| 0 423 695 | 4/1991 | European Pat. Off. . |
| 0 561 166 | 9/1993 | European Pat. Off. . |

OTHER PUBLICATIONS

WPIDS AN 88–072 668, Axelsson et al, 1988.

*Primary Examiner*—Rebecca Cook
*Attorney, Agent, or Firm*—Bacon & Thomas PLLC.

[57] ABSTRACT

This invention relates to aerosol formulations of use for the administration of medicaments by inhalation and in particular to a pharmaceutical aerosol formulation which comprises (a) particulate medicament; (b) at least one sugar; and (c) a fluorocarbon or hydrogen-containing chlorofluorocarbon propellant. A method of treating respiratory disorders which comprises administration by inhalation of an effective amount of a pharmaceutical aerosol formulation as defined is also described.

31 Claims, No Drawings

PHARMACEUTICAL AEROSOL CONTAINING AT LEAST ONE SUGAR

This is a 371 of PCT/EP95/05085 filed Dec. 22, 1995.

This invention relates to aerosol formulations of use for the administration of medicaments by inhalation.

The use of aerosols to administer medicaments has been known for several decades. Such aerosols generally comprise the medicament, one or more chlorofluorocarbon propellants and either a surfactant or a solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP 0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

Surprisingly, the applicants have now found that particular sugars may advantageously be used to prepare novel aerosol formulations.

Thus, one aspect of the invention provides an aerosol formulation comprising:

a) particulate medicament;
b) at least one sugar; and
c) a fluorocarbon or hydrogen-containing chlorofluorocarbon propellant.

In an alternative embodiment the present invention provides a pharmaceutical aerosol formulation as hereinbefore defined with the provisos that when said formulation consists essentially of human insulin, soybean lecithin S100, lactose and heptafluoropropane the weight to weight ratio of medicament to lactose is other than 1:1 and that when said formulation consists essentially of salbutamol, soybean lecithin S100, lactose and heptafluoropropane the weight to weight ratio of medicament to lactose is other than 200:1798.

The particle size of the particulate (e.g. micronised) medicament should be such as to permit substantially all of the particles to be potentially available for inhalation into the lungs upon administration of the powder composition. Thus, for example, at least 90%, preferably at least 95% by weight of the particles will have a diameter of less than 15 micrometers, preferably in the range of 1 to 10 micrometers, for example 1 to 5 micrometers.

The final aerosol formulation desirably contains 0.005–10% w/w, preferably 0.005–5% w/w, especially 0.01–1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. dilfiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, orciprenaline, or (−)4-amino-3,5-dichloro-α-[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred medicaments for administration using aerosol formulations in accordance with the invention include antiallergics, bronchodilators and antiinflammatory steroids of use in the treatment of respiratory disorders such as asthma by inhalation therapy, for example cromoglycate (e.g. as the sodium salt), salbutamol (e.g. as the free base or the sulphate salt), salmeterol (e.g. as the xinafoate salt), terbutaline (e.g. as the sulphate salt), reproterol (e.g. as the hydrochloride salt), a beclomethasone ester (e.g. the diproprionate), a fluticasone ester (e.g. the propionate) or (−)4-amino-3,5-dichloro-α-[[[6-[2-[2-pyridinyl)ethoxy]hexyl]amino]methyl]benzenemethanol. Salmeterol, especially salmeterol xinafoate, salbutamol, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly the present invention further provides aerosol formulations in accordance with the invention which contain two or more particulate medicaments. Thus suitable combinations of bronchodilatory agents include ephedrine and theophylline, fenoterol and ipratropium, and isoetharine and phenylephrine aerosol formulations.

Preferred aerosol formulations in accordance With the invention comprise (a) an effective amount of a particulate bronchodilator medicament, (b) an effective amount of a particulate antiinflammatory, preferably a steroidal antiinflammatory medicament, (c) a fluorocarbon or hydrogen— containing chlorofluorocarbon propellant, and (d) at least one sugar. Particularly preferred aerosol formulations contain bronchodilators such as salbutamol (e.g. as the free base or as the sulphate salt), salmeterol (e.g. as the xinafoate salt)

or isoprenaline in combination with an antiinflammatory steroid such as a beclomethasone ester (e.g. the diprionate) or a fluticasone ester (e.g. the propionate). Alternatively aerosol formulations may contain a bronchodilator in combination with an antiallergic such as cromoglycate (e.g. the sodium salt). Combinations of isoprenaline and sodium cromoglycate, salmeterol and fluticasone propionate, or salbutamol and beclomethasone dipropionate are especially preferred.

The aerosol formulations according to the present invention desirably contain 0.0001 to 50% w/w, preferably 0.001 to 20, for example 0.001 to 1% of sugar relative to the total weight of the formulation. Generally the ratio of medicament:sugar falls within the range of 1:0.01 to 1:100 preferably 1:0.1 to 1:10.

The particle size of the sugars used in the formulations of the present invention can be selected as desired using conventional techniques such as milling or micronisation. However, preferably the sugars will have a particle size of less than about 100 microns such as less than about 70 microns, for example, less than 20 microns. Typical sugars which may be used in the formulations include, for example, sucrose, lactose and dextrose, preferably lactose, and reducing sugars such as mannitol and sorbitol.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$ hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chlorofluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$ hydrogen-containing fluorocarbons such as 1,1,1,2-tetrafluoroethane($CF_3CH_2F$) and 1,1,1,2,3,3,3-heptafluoro-n-propane ($CF_3CHFCF_3$).

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

The propellant may optionally contain an adjuvant having a higher polarity and/or a higher boiling point than the propellant. Polar adjuvants which may be used include (e.g. $C_{2-6}$) aliphatic alcohols and polyols such as ethanol, isopropanol and propylene glycol, preferably ethanol. In general only small quantities of polar adjuvants (e.g. 0.05–3.0% w/w based upon the propellant) may be required to improve the stability of the dispersion—the use of quantities in excess of 5% w/w may tend to dissolve the medicament. Formulations in accordance with the invention may preferably contain less than 1 % w/w, e.g. about 0.1% w/w, of polar adjuvant. However, the formulations of the invention are preferably substantially free of polar adjuvants, especially ethanol Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated $C_{1-6}$ hydrocarbon.

Optionally, the aerosol formulations according to the invention may further comprise one or more surfactants. The surfactants must be physiologically acceptable upon administration by inhalation. Within this category are included surfactants such as oleic acid, sorbitan trioleate (Span® 85), sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil and sunflower seed oil. Preferred surfactants are lecithin, oleic acid and sorbitan trioleate.

An alternative class of surfactants are described in EP 0478686, especially surfactants of formula (I)

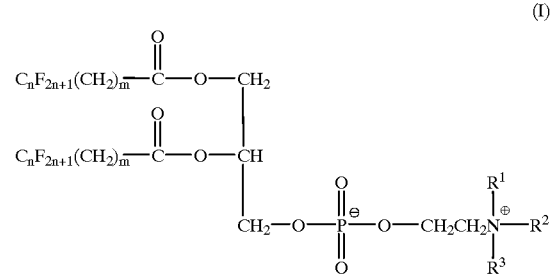

wherein n is an integer of 1 to 18, especially 2 to 12; m is an integer of 0 to 17, especially 0 to 11; and $R^1$, $R^2$ and $R^3$ are each independently a hydrogen atom or a $C_{1-4}$ alkyl group.

Particularly preferred surfactants of formula (I) are the fluorinated phosphatidylcholines wherein $R^1$, $R^2$ and $R^3$ each represent methyl, n is an integer of 4 to 8, especially 4 or 6, and m is an integer of 4 to 10, especially 4 or 6.

If desired, the surfactant may be incorporated into the aerosol formulation in the form of a surface coating on the particulate medicament. In this case, the use of substantially non-ionic surfactants which have reasonable solubility in substantially non-polar solvents is frequently advantageous since it facilitates coating of the medicament particles using solutions of surfactant in non-polar solvents in which the medicament has limited or minimal solubility.

The amount of surfactant employed in coating the particulate medicament is desirably in the range 0.1 to 10% w/w, preferably 1 to 10% w/w, relative to the medicament. Where the surfactant is present as a surface coating, the amount may advantageously be chosen such that a substantially monomolecular coating of surfactant is formed. However, it is preferable that the formulations of the invention are substantially free of surfactants, i.e contain less than an effective stabilising amount of a surfactant such as less than 0.0001% by weight of medicament.

The formulations according to the present invention may optionally contain one or more further excipients or carriers conventionally used in the art of pharmaceutical aerosol formulation. Such optional excipients include, but are not limited to, taste masking agents, buffers, antioxidants, water and chemical stabilisers.

A particularly preferred embodiment of the invention provides a pharmaceutical aerosol formulation consisting essentially of one or more particulate medicament, particulate lactose and one or more fluorocarbon or hydrogen-containing chlorofluorocarbon propellant.

The formulations of the invention may be prepared by dispersal of the medicament and sugar e.g lactose in the selected propellant in an appropriate container, e.g. with the aid of mixing. Alternatively, the sugar may be pre-filled into canisters suitable for delivering aerosol formulations before filling with the medicament in the selected propellant. The process is desirably carried out under anhydrous conditions to obviate any adverse effects of moisture on suspension stability.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention is particularly impressive and may be measured by conventional techniques, for example by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204–207, Appendix XVII C.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak pic, UK (e.g. BK300, BK357) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament and sugar may or may not be pre-blended and then added to one or more charge vessels. Liquified propellant is pressure-filled through the charge vessel(s) into a manufacturing vessel. The medicament and sugar suspension is mixed before recirculation to a filling machine and an aliquot of the medicament and sugar suspension is then filled through the metering valve of the canister.

Alternatively the sugar may be mixed with the selected propellant in a suitable vessel and then added to the canister either before or after the medicament suspension is added to the canister.

Alternatively, the sugar and optionally the medicament may be pre-filled into the empty canisters before the propellant is filled into the canisters.

Alternatively, the sugar may be coated onto the empty canisters by dissolving or dispersing the sugar in a suitable liquid, for example a solvent for the sugar such as water or methanol, or a non-solvent for the sugar such as acetone or hexane, and adding to the empty canister. After orientation to ensure that the solution or dispersion covers the interior surfaces of the canister, the liquid may be evaporated off leaving a coat of sugar on the interior surfaces of the canister. The canister is then filled with medicament in the selected propellant.

Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Suitable daily doses, may be, for example in the range 50 to 200 microgram of salmeterol, 100 to 1000 microgram of salbutamol, 50 to 2000 microgram of fluticasone propionate or 100 to 2000 microgram of beclomethasone dipropionate, depending on the severity of the disease.

Thus, for example, each valve actuation may deliver 25 microgram salmeterol, 100 microgram salbutamol, 25, 50, 125 or 250 microgram fluticasone propionate or 50, 100, 200 or 250 microgram beclomethasone dipropionate. Typically each filled canister for use in a metered dose inhaler contains 50, 80, 100, 120, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The following non-limitative Examples serve to illustrate the invention.

EXAMPLE 1

Particulate lactose was dispensed into clean, dry glass bottle. The metering valve was fitted onto the bottles and micronised fluticasone propionate, mixed with 1,1,1,2-tetrafluoroethane was pressure-filled into the canisters through the metering valve. The resultant inhalers delivered 25 microgram of fluticasone propionate (ex-valve) per actuation. The ratio of medicament:lactose was 1:10. The proportion of lactose was 0.33% of the total fill weight of the inhaler.

EXAMPLE 2

Particulate lactose was dispensed into clean, dry aluminium aerosol canisters. The metering valve was fitted onto the canisters and micronised fluticasone propionate, mixed with 1,1,1,2-tetrafluoroethane was pressure-filled into the canisters through the metering valve. 1,1,1,2-Tetrafluoroethane was then pressure-filled into the canisters through the metering valve. The resultant inhalers delivered 50 microgram of fluticasone propionate (ex-valve) per actuation. The ratio of medicament:lactose was 1:1. The proportion of lactose was 0.067% of the total fill weight of the inhaler.

EXAMPLE 3

Particulate lactose was dispensed into clean, dry aluminium aerosol canisters. The metering valve was fitted onto the canisters and micronised fluticasone propionate, mixed with 1,1,1,2-tetrafluoroethane was pressure-filled into the canisters through the metering valve. 1,1,1,2-Tetrafluoroethane was then pressure-filled into the canisters through the metering valve. The resultant inhalers delivered 50 microgram of fluticasone propionate (ex-valve) per actuation. The ratio of medicament:lactose was 1:5. The proportion of lactose was 0.33% of the total fill weight of the inhaler.

EXAMPLE 4

Particulate lactose and micronised fluticasone propionate were mixed with 1,1,1,2-tetrafluoroethane and pressure-filled into clean, dry aluminium canisters fitted with a metering valve. 1,1,1,2-Tetrafluoroethane was then pressure filled into the canisters through the metering valve. The resultant inhalers delivered 25 microgram of fluticasone propionate (ex-valve) per actuation. The ratio of medicament:lactose was 1:5. The proportion of lactose was 0.167% of the total fill weight of the inhaler.

EXAMPLE 5

Particulate lactose and micronised fluticasone propionate were mixed with 1,1,1,2-tetrafluoroethane and pressure-filled into clean, dry aluminium canisters fitted with a metering valve. 1,1,1,2-Tetrafluoroethane was then pressure filled into the canisters through the metering valve. The resultant inhalers delivered 50 microgram of fluticasone propionate (ex-valve) per actuation. The ratio of medicament:lactose was 1:1. The proportion of lactose was 0.067% of the total fill weight of the inhaler.

EXAMPLE 6

Particulate lactose and micronised fluticasone propionate were mixed with 1,1,1,2-tetrafluoroethane and pressure-filled into clean, dry aluminium canisters fitted with a metering valve. 1,1,1,2-Tetrafluoroethane was then pressure filled into the canisters through the metering valve. The resultant inhalers delivered 50 microgram of fluticasone propionate (ex-valve) per actuation. The ratio of medicament:lactose was 1:5. The proportion of lactose was 0.333% of the total fill weight of the inhaler.

EXAMPLE 7

Particulate lactose and micronised fluticasone propionate were mixed with 1,1,1,2-tetrafluoroethane and pressure-filled into clean, dry aluminium canisters fitted with a metering valve. 1,1,1,2-Tetrafluoroethane was then pressure filled into the canisters through the metering valve. The resultant inhalers delivered 50 microgram of fluticasone propionate (ex-valve) per actuation. The ratio of medicament:lactose was 1:8. The proportion of lactose was 0.533% of the total fill weight of the inhaler.

EXAMPLE 8

Particulate lactose and micronised fluticasone propionate were mixed with 1,1,1,2-tetrafluoroethane and pressure-filled into clean, dry aluminium canisters fitted with a metering valve. 1,1,1,2-Tetrafluoroethane was then pressure filled into the canisters through the metering valve. The resultant inhalers delivered 25 microgram of fluticasone propionate (ex-valve) per actuation. The ratio of medicament:lactose was 1:5. The proportion of lactose was 0.167% of the total fill weight of the inhaler.

EXAMPLE 9

Particulate lactose was dispensed in to clean, dry aluminium aerosol canisters. The metering valve was fitted on to the canisters and micronised salmeterol xinafoate, mixed with 1,1,1,2-tetrafluoroethane was pressure-filled in to the canisters through the metering valve. 1,1,1,2-Tetrafluoroethane was then pressure-filled in to the canisters through the metering valve. The resultant inhalers delivered 25 microgram of salmeterol (ex-valve) per actuation. The ratio of medicament:lactose was 1:1. The proportion of lactose was 0.053% of the total fill weight of the inhaler.

EXAMPLE 10

Particulate lactose was dispensed in to clean, dry aluminium aerosol canisters. The metering valve was fitted on to the canisters and micronised salmeterol xinafoate, mixed with 1,1,1,2-tetrafluoroethane was pressure-filled in to the canisters through the metering valve. 1,1,1,2-Tetrafluoroethane was then pressure-filled in to the canisters through the metering valve. The resultant inhalers delivered 25 microgram of salmeterol (ex-valve) per actuation. The ratio of medicament:lactose was 1:5. The proportion of lactose was 0.266% of the total fill weight of the inhaler.

EXAMPLE 11

Particulate sucrose was dispensed in to clean, dry aluminium aerosol canisters. The metering valve was fitted on to the canisters and micronised salmeterol xinafoate, mixed with 1,1,1,2-tetrafluoroethane was pressure-filled in to the canisters through the metering valve. 1,1,1,2-Tetrafluoroethane was then pressure-filled in to the canisters through the metering valve. The ratio of medicament:sucrose was 1:1. The proportion of sucrose was 0.266% of the total fill weight of the inhaler.

EXAMPLE 12

Particulate dextrose was dispensed in to clean, dry aluminium aerosol canisters. The metering valve was fitted on to the canisters and micronised salmeterol xinafoate, mixed with 1,1,1,2-tetrafluoroethane was pressure-filled in to the canisters through the metering valve. 1,1,1,2-Tetrafluoroethane was then pressure-filled in to the canisters through the metering valve. The ratio of medicament:dextrose was 1:5. The proportion of dextrose was 0.266% of the total fill weight of the inhaler.

EXAMPLE 13

Particulate mannitol was dispensed in to clean, dry aluminium aerosol canisters. The metering valve was fitted on to the canisters and micronised salmeterol xinafoate, mixed with 1,1,1,2-tetrafluoroethane was pressure-filled in to the canisters through the metering valve. 1,1,1,2-Tetrafluoroethane was then pressure-filled in to the canisters through the metering valve. The ratio of medicament:mannitol was 1:5. The proportion of mannitol was 0.266% of the total fill weight of the inhaler.

EXAMPLE 14

Particulate lactose is blended with salmeterol xinafoate and the blend is mixed with 1,1,1,2-tetrafluoroethane and pressure-filled in to clean, dry aluminium canisters fitted with a metering valve, through the metering valve. 1,1,1,2-Tetrafluoroethane is then pressured-filled in to the canisters through the metering valve. The ratio of medicament:lactose was 1:1. The proportion of lactose was 0.053% of the total fill weight of the inhaler.

EXAMPLE 15

Particulate lactose is blended with salmeterol xinafoate and the blend is mixed with 1,1,1,2-tetrafluoroethane and pressure filled in to clean, dry aluminium canisters fitted with a metering valve, through the metering valve. 1,1,1,2-Tetrafluoroethane is then pressure-filled in to the canisters through the metering valve. The ratio of medicament:lactose was 1:5. The proportion of lactose was 0.266% of the total fill weight of the inhaler.

EXAMPLE 16

Particulate lactose is blended with salmeterol xinafoate and the blend is mixed with 1,1,1,2-tetrafluoroethane and pressure-filled in to clean, dry aluminium canisters fitted with a metering valve, through the metering valve. 1,1,1,2-tetrafluoroethane is then pressured-filled in to the canisters through the metering valve. The ratio of medicament:lactose was 1:10. The proportion of lactose was 0.532% of the total fill weight of the inhaler.

EXAMPLE 17

Particulate lactose is blended with micronised fluticasone propionate and the blend is mixed with 1,1,1,2-tetrafluoroethane and pressure-filled into clean, dry aluminium canisters fitted with a metering valve, through the metering valve. 1,1,1,2-Tetrafluoroethane is then pressure-filled into the canisters through the metering valve. The resultant inhalers deliver 25 microgram of fluticasone propionate (ex-valve) per actuation. The ratio of medicament:lactose is 1:1. The proportion of lactose is 0.033% of the total fill weight of the inhaler.

EXAMPLE 18

Particulate lactose is mixed with 1,1,1,2-tetrafluoroethane and added to clean, dry aluminium aerosol canisters fitted with a metering valve. Micronised fluticasone propionate is mixed with 1,1,1,2-tetrafluoroethane and pressure-filled into the canisters through the metering valve. 1,1,1,2-Tetrafluoroethane is then pressure-filled into the canisters through the metering valve. The resultant inhalers deliver 25 microgram of fluticasone propionate (ex-valve) per actuation The ratio of medicament:lactose is 1:1. The proportion of lactose is 0.033% of the total fill weight of the inhaler.

EXAMPLE 19

Particulate lactose is dispensed into clean, dry aluminium aerosol canisters. The metering valve is fitted onto the canisters and micronised fluticasone propionate, mixed with 1,1,1,2-tetrafluoroethane is pressure-filled into the canisters through the metering valve. 1,1,1,2-Tetrafluoroethane is then pressure-filled into the canisters through the metering valve. The resultant inhalers deliver 25 microgram of fluticasone propionate (ex-valve) per actuation. The ratio of medicament:lactose is 1:1. The proportion of lactose is 0.033% of the total fill weight of the inhaler.

EXAMPLE 20

Particulate lactose is dissolved in water/ethanol/methanol or a mixture thereof and added to clean, dry aluminium aerosol canisters. The canister is orientated such that the walls are coated with the solution. The solvent is evaporated off leaving a coating of lactose on the walls of the canister. Micronised fluticasone propionate, mixed with 1,1,1,2-tetrafluoroethane is pressured-filled into the canisters through the metering valve. 1,1,1,2-Tetrafluoroethane is then pressure-filled into the canisters through the metering valve. The resultant inhalers deliver 25 microgram of fluticasone propionate (ex-valve) per actuation. The ratio of medicament:lactose is 1:1. The proportion of lactose is 0.033% of the total fill weight of the inhaler.

EXAMPLE 21

Particulate lactose is dispersed in a suitable non-solvent for lactose, for example acetone, and added to clean, dry aluminium aerosol canisters. The canister is orientated such that the walls are coated with the dispersion. The non-solvent is evaporated off leaving a coating of lactose on the walls of the canister. Micronised fluticasone propionate, mixed with 1,1,1,2-tetrafluoroethane is pressure-filled into the canisters through the metering valve. 1,1,1,2-Tetrafluoroethane is then pressure-filled into the canisters through the metering valve. The resultant inhalers deliver 25 microgram of fluticasone propionate (ex-valve) per actuation. The ratio of medicament:lactose is 1:1. The proportion of lactose is 0.033% of the total fill weight of the inhaler.

EXAMPLES 22–41

Aerosols are prepared as described in Examples 17 to 21 but containing 50 microgram per actuation fluticasone propionate (Examples 22 to 26), salmeterol 25 microgram per actuation (Examples 27 to 31), salbutamol 100 microgram per actuation (Examples 32 to 36) or beclomethasone dipropionate 50 microgram per actuation (Examples 37 to 41) in place of fluticasone propionate.

EXAMPLES 42–46

Aerosols are prepared as described in Examples 17 to 21 but with 1:5 ratio of medicament:lactose. The proportion of lactose is 0.167% of the total fill weight of the inhaler.

EXAMPLES 47–51

Aerosols are prepared as described in Examples 17 to 21 but with 1:10 ratio of medicament:lactose. The proportion of lactose is 0.33% of the total fill weight of the inhaler.

EXAMPLES 52–56

Aerosols are prepared as described in Examples 17 to 21 but with 1:0.1 ratio of medicament:lactose. The proportion of lactose is 0.0033% of the total fill weight of the inhaler.

EXAMPLES 57–104

Aerosols are prepared as described in Examples 42 to 56 but containing 50 microgram per actuation fluticasone propionate (Examples 57 to 72), 25 microgram per actuation salmeterol (Examples 73 to 88) and 100 microgram per actuation salbutamol (Examples 89 to 104).

EXAMPLES 105–129

Aerosols are prepared as described in Examples 17 to 41 but containing 1,1,1,2,3,3,3-heptafluoro-n-propane as propellant in place of 1,1,1,2-tetrafluoroethane.

EXAMPLES 130–144

Aerosols are prepared as described in Examples 7 to 21 but containing dextrose (Examples 130 to 134), sucrose (Examples 135 to 139) or mannitol (Examples 140 to 144) in place of lactose.

I claim:

1. A pharmaceutical aerosol formulation comprising
   (a) a particulate medicament selected from the group consisting of salmeterol xinafoate, salbutamol sulphate, fluticasone propionate, beclomethasone dipropionate, formeterol, cromoglycate, terbutaline, reproterol, (-)-4-amino-3,5-dichloro-α-[[[6-[2-(2-pyridinyl)ethoxy]hexyl]amino]methyl]benzenemethanol, budesonide, triamcinolone acetonide, a physiologically acceptable salt, a solvate or a mixture thereof;
   (b) at least one sugar; and
   (c) a propellant selected from the group consisting of a hydrogen-containing fluorocarbon propellant, a perfluorocarbon propellant and a hydrogen-containing chlorofluorocarbon propellant which formulation is substantially free of surfactant.

2. A formulation according to claim 1 comprising 0.0001 to 50% w/w of sugar relative to the total weight of the formulation.

3. A formulation according to claim 2 comprising 0.001 to 20% w/w of sugar relative to the total weight of the formulation.

4. A formulation according to claim 1 wherein the propellant comprises 1,1,1,2-tetrafluoroethane, 1,1,1,2,3,3,3-heptafluoro-n-propane or a mixture thereof.

5. A formulation according to claim 1 wherein the medicament is a bronchodilator or an anti-inflammatory steroid.

6. A formulation according to claim 1 wherein the medicament is salmeterol xinafoate.

7. A formulation according to claim 1 wherein the medicament is salbutamol sulphate.

8. A formulation according to claim 1 wherein the medicament is fluticasone propionate.

9. A formulation according to claim 1 wherein the medicament is beclomethasone dipropionate or a physiologically acceptable solvate thereof.

10. A formulation according to claim 1 wherein the medicament is formeterol, cromoglycate, terbutaline, reproterol or (-)4amino-3,5-dichloro-α-[[[6-[2-(2-pyridinyl)ethoxy]hexyl]amino]methyl]benzemethanol budesonide, triamcinolone acetonide or a physiologically acceptable salt or solvate thereof.

11. A formulation according to claim 1 wherein the medicament is present in an amount of 0.005 to 10% w/w relative to the total weight of the formulation.

12. A formulation according to claim 11 wherein the medicament is present in an amount of 0.01 to 1% w/w relative to the total weight of the formulation.

13. A formulation according to claim 1 which comprises two or more particulate medicaments.

14. A formulation according to claim 13 which comprises salbutamol or salmeterol or a physiologically acceptable salt thereof in combination with an anti-inflammatory steroid.

15. A formulation according to claim 14 which comprises salmeterol or salbutamol or a physiologically acceptable salt thereof in combination with fluticasone propionate or beclomethasone dipropionate or a physiologically acceptable solvate thereof.

16. A formulation according to claim 1 comprising an adjuvant having a higher polarity and a boiling point than the propellant.

17. A formulation according to claim 16 wherein the adjuvant having a higher polarity than the propellant is present in an amount of 0.05 to 5% w/w based upon the propellant.

18. A formulation according to claim 1 comprising a surfactant.

19. A formulation according to claim 1 wherein said formulation is substantially free of surfactant.

20. A canister suitable for delivering a pharmaceutical aerosol formulation which comprises a container capable of withstanding the vapour pressure of the propellant used which container is closed with a metering valve and contains a pharmaceutical aerosol formulation according to claim 1.

21. A canister according to claim 20 wherein the container is a metal can.

22. A canister according to claim 21 wherein the container is an aluminium can.

23. A canister according to claim 21 wherein the container is plastics-coated.

24. A metered dose inhaler which comprises a canister according to claim 20 fitted into a suitable channelling device.

25. A formulation according to claim 1 further comprising an adjuvant having a higher polarity or a boiling point than the propellant.

26. A pharmaceutical aerosol formulation consisting essentially of
    (a) A particulate medicament selected from the group consisting of salmeterol xinafoate, salbutamol sulphate, fluticasone propionate, beclomethasone dipropionate, formeterol, cromoglycate, terbutaline, reproterol, (-)4-amino-3,5-dichloro-α-[[[6-[2-(2-pyridinyl)ethoxy]hexyl]amino]methyl]benzenemethanol, budesonide, triamcinolone acetonide, a physiologically acceptable salt, a solvate, or a mixture thereof;
    (b) at least one sugar; and
    (c) a propellant selected from the group consisting of a hydrogen-containing fluorocarbon propellant, a perfluorocarbon propellant and a hydrogen-containing chlorofluorocarbon propellant.

27. A canister suitable for delivering a pharmaceutical aerosol formulation which comprises a container capable of withstanding the vapour pressure of the propellant used which container is closed with a metering valve and contains a pharmaceutical aerosol formulation according to claims 26.

28. A canister according to claim 27 wherein the container is a metal can.

29. A canister according to claim 27 wherein the container is an aluminum can.

30. A canister according to claim 27 wherein the container is plastics-coated.

31. A metered dose inhaler which comprises a canister according to claim 27 fitted into a suitable channeling device.

* * * * *